United States Patent [19]

Alder

[11] Patent Number: 4,990,232

[45] Date of Patent: Feb. 5, 1991

[54] PROCESS FOR THE PREPARATION OF CARBODIIMIDES

[75] Inventor: Alex Alder, Arisdorf, Switzerland

[73] Assignee: Ciba-Geigy Corporation, Ardsley, N.Y.

[21] Appl. No.: 240,166

[22] Filed: Sep. 2, 1988

[30] Foreign Application Priority Data

Sep. 9, 1987 [CH] Switzerland ............. 3483/87-5

[51] Int. Cl.$^5$ ............................................. C07C 209/80
[52] U.S. Cl. ................................. 204/157.81; 564/252
[58] Field of Search ................. 564/252; 204/157.81, 204/DIG. 912

[56] References Cited

U.S. PATENT DOCUMENTS 2,656,383  10/1953  Schmidt et al. ............ 564/252

OTHER PUBLICATIONS

Dubey et al., Current Science, vol. 54, No. 7 (1985); pp. 340–342.

*Primary Examiner*—Robert A. Wax
*Assistant Examiner*—F. Tsung
*Attorney, Agent, or Firm*—Edward McC. Roberts

[57] ABSTRACT

The photooxidation of N,N'-substituted thioureas with oxygen in the presence of an acid-trapping agent gives N,N'-substituted carbodiimides. The carbodiimides can be converted into cyanoguanidines, which are suitable as latent curing agents for epoxy resins.

13 Claims, No Drawings

PROCESS FOR THE PREPARATION OF CARBODIIMIDES

The invention relates to a process for the preparation of carbodiimides by photooxidation of N,N'-substituted thioureas with oxygen in the presence of an acid-trapping agent.

The preparation of N,N-substituted carbodiimides by desulfurization of thioureas with, for example, metal oxides (HgO, Ag₂O or PbO) is described in Organic Chemistry, Organic Functional Group Preparations, Vol. 12-II, pages 233 to 259. The desulfurization can also be carried out with alkali metal hypochlorites in aqueous-alkaline solution (see also DE-A-823,445).

R. Dubey et al. describe the photooxidation of N,N'-diphenylurea with singlet oxygen in methanolic solution in Current Science, Vol. 54, No. 7, pages 340–342 (1985). 1-Nitrobenzyl hydroperoxide is formed here.

It has been found that carbodiimides are obtained if the photooxidation of N,N'-substituted ureas is carried out in the presence of an acid-trapping agent.

The invention relates to a process for the preparation of carbodiimides of the formula I

$$R-N=C=N-R^1 \qquad (I),$$

in which R and R¹ independently of one another are linear or branched $C_1$–$C_{20}$alkyl, $C_2$–$C_{18}$alkenyl or $C_2$–$C_{18}$alkynyl; $C_3$–$C_{10}$cycloalkyl or -cycloalkenyl, heterocycloalkyl or heterocycloalkenyl which has 3 to 10 ring atoms and is bonded via a C atom, a polycyclic hydrocarbon radical with 6 to 10 C atoms, $C_6$–$C_{14}$aryl, $C_7$–$C_{20}$aralkyl, heteroaryl with 5 or 6 ring atoms or heteroaralkyl with 5 or 6 ring atoms and 1 to 6 C atoms in the alkyl group, which are unsubstituted or substituted by $C_1$–$C_{12}$alkyl, -alkoxy or -alkylthio, $C_3$–$C_6$cycloalkyl, -cycloalkoxy or -cycloalkylthio, $C_6$–$C_{10}$aryl, -aryloxy or -arylthio, $C_7$–$C_{16}$aralkyl, -aralkoxy or -aralkylthio, heteroaryl or heteroaryloxy with 5 or 6 ring atoms, cyano, halogen, $C_2$–$C_{24}$secondary amino, —C(O)OR², —O(O)CR⁴, —NR²(O)CR⁴, —C(O)NR²R³, in which R² is $C_1$–$C_{12}$alkyl phenyl or benzyl R³ is H or is as defined for R² and R⁴ is as defined for R², it being possible for the substituents alkyl, alkoxy and alkylthio in turn to be substituted by $C_1$–$C_{12}$alkoxy, halogen, cyano, $C_2$–$C_{24}$secondary amino, —C(O)OR², —O-(O)CR⁴, —NR²(O)CR⁴, —C(O)NR²R³, cycloalkyl or heterocycloalkyl with 4–8 ring C atoms or 5 or 6 ring atoms, and for the substituents cycloalkyl, cycloalkoxy, cycloalkylthio, aryl, aryloxy, arylthio, aralkyl, aralkoxy, aralkylthio, heteroaryl or heteroaryloxy to be substituted by $C_1$–$C_{12}$alkyl, -alkoxy or -alkylthio, halogen, cyano, $C_2$–$C_{24}$secondary amino, —C(O)OR², —O-(O)CR⁴, —NR²(O)CR⁴ or —C(O)NR²R³, and for cycloalkyl, cycloalkenyl, heterocycloalkyl or heterocycloalkenyl R and R¹ to be fused with $C_6$–$C_{14}$aryl or heteroaryl with 5 or 6 ring atoms, by photooxidation of a thiourea of the formula II

$$\underset{R-HN-C-NH-R^1,}{\overset{S}{\|}} \qquad (II)$$

in which R and R¹ are as defined above, with oxygen in a solvent, which comprises carrying out the reaction in the presence of an acid-trapping agent which is soluble in the reaction medium.

R and R¹ can be linear or branched alkyl with preferably 1 to 12, in particular 1 to 6 C atoms. Examples are methyl, ethyl, n- or i-propyl, n-, i- or t-butyl, 1-, 2- or 3-pentyl, 1-, 2- or 3-hexyl, 1-, 2-, 3- or 4-heptyl, 1-, 2-, 3- or 4-octyl, nonyl, decyl, undecyl, dodecyl, tetradecyl, hexadecyl, octadecyl and eicosyl. In a preferred embodiment, R and R¹ are α-branched alkyl.

R and R¹ can be linear or branched alkenyl with preferably 2 to 12, in particular 2 to 6, C atoms. This can correspond, for example, to $C_2$–$C_{17}$alkenyl-$C_1$–$C_{16}$alkyl with a total of 18 C atoms. The alkenyl group can preferably contain 2–11 and in particular 2–5 C atoms, and the alkyl group can preferably contain 1–10 and in particular 1–4 C atoms. Examples are: allyl, but-1-en-3-yl, but-1-en-4-yl, but-2-en-4-yl, pent-1-en-5-yl, pent-1-en-4-yl, pent-1-en-3-yl, pent-2-en-4-yl, pent-3-en-5-yl, hex-1-en-6-yl, hex-2-en-6-yl, hex-3-en-6-yl, hex-3-en-2-yl, hex-3-en-5-yl, heptenyl, octenyl, nonenyl, decenyl, undecenyl, dodecenyl, tetradecenyl, hexadecenyl and octadecenyl.

R and R¹ can be linear or branched alkynylalkyl with preferably 2 to 12, in particular 2 to 6, C atoms. This can be, for example, $C_2$–$C_{17}$-alkynyl-$C_1$–$C_{16}$alkyl with a total of 18 C atoms. The alkynyl group can preferably contain 2–11 and in particular 2–5 C atoms and the alkyl group can preferably contain 1–10 and in particular 1–4 C atoms. Examples are propargyl, but-1-in-3-yl, but-2-in-4-yl, pent-3-in1-yl, pent-1-in-3-yl, pent-1-in-4-yl, pent-1-in-5-yl, pent-2-in-4-yl, pent-2-in-5-yl, hex-1-in-3-yl or -4-yl or -5-yl or -6-yl, hex-2-in-4-yl or -5-yl, or -6-yl, hex-3-in-5-yl or -6-yl, heptinyl, octinyl, noninyl, decinyl, undecinyl, dodecinyl, tetradecinyl, hexadecinyl and octadecinyl.

R and R¹ can be cycloalkyl or cycloalkenyl which preferably has 4 to 8, in particular 5 or 6, ring C atoms and is unfused or fused with $C_6$–$C_{14}$aryl, preferably benzene, or with heteroaryl with 5 or 6 ring atoms. Examples are cyclopropyl, cyclobutyl, cyclopentyl, cyclohexyl, cycloheptyl, cyclooctyl, cyclodecyl, cycloprop-1-en-3-yl, cyclobut-1-en-3-yl, cyclopent-1-en-3-yl, cyclopent-1-en-4-yl, cyclohex-1-en-3-yl, cyclohex-1-en-4yl, cyclopentenyl, cyclooctenyl and cyclodecenyl.

R and R¹ can be heterocycloalkyl or heterocycloalkenyl which is unfused or fused with $C_6$–$C_{14}$aryl, in particular benzene, or with heteroaryl with 5 or 6 ring atoms, or heteroaryl, it being possible for these radicals to contain, for example, heteroatoms from the group comprising O, S and N. The N atom is a tertiary N atom. If the N atom is present in the ring as a secondary amine group, this N atom is, for example, $C_1$–$C_{12}$—, in particular $C_1$–$C_4$alkylated, phenylated or benzylated. It can also contain protective groups, for example $C_1$–$C_4$alkoxymethyl or $R_3^5$Si groups, in which R⁵ is $C_1$–$C_{12}$alkyl. These heterocyclic radicals preferably contain 1 to 3, in particular 1 or 2, identical or different heteroatoms. The heterocycloalkyl or -alkenyl preferably contains 5 or 6 ring members. ! Examples of heterocyclic radicals from which R and R¹ can be derived are (protective groups for secondary N groups are not mentioned): pyrrolidine, tetrahydrofuran, tetrahydrothiophene, pyrroline, dihydrofuran, dihydrothiophene, indane, dihydrocoumaron, dihydrobenzothiophene, carbazole, dibenzofuran, dibenzothiophene, pyrazolidine, imidazolidine, pyrazoline, imidazoline, benzimidazolidine, oxazolidine, oxazoline, thiazolidine, isooxazolidine, isooxazoline, isothiazolidine, isothiazoline, benzoxazolidine, benzisooxazolidine, benzthiazolidine, 1,2,3- or 1,2,4-triazolidine, 1,2,3- or 1,2,4-triazoline, 1,2,3,- or 1,2,4-oxazolidine or -oxazoline, piperidine, di- and tetrahydropyridine, dihydro- and tetrahydropyran, di- and tetrahydrothiopyran, piperazine, dehydropiperazine, morpholine, thiomorpholine, 1,3- and 1,4-dioxane, 1,4-dithiane, azepan, 1,3-dioxolane, 1,3-dithiolane, pyrrole, indole, imidazole, benzimidazole, furan, thiophene, benzofuran, benzothiophene, carbazole, dibenzofuran, dibenzothiophene, oxazole, isooxazole, thiazole, isothiazole, benzoxazole, benzothiazole, pyridine, pyrimidine, pyrazine, pyridazine, quinoline, isoquinoline, acridine, chromene, chromane, pyran, thiapyran, phenazine, phenoxazine, phenolthiazine and purine. Heterocyclic radicals R and $R^1$ are bonded to the N atoms in formula I via a C atom.

R and $R^1$ can be a polycyclic hydrocarbon radical with 6 to 10 C atoms. Examples of such hydrocarbons from which R and $R^1$ can be derived are: bicyclo-[0,0,3]-hexane, bicyclo-[1,0,3]-hexane, bicyclo-[2,2,1]-heptane, bicyclo-[2,2,1]-heptene, bicyclo-[2,2,2]-octane and bicyclo-[2,2,2]-octene.

R and $R^1$ can be $C_6$-$C_{14}$aryl. Examples are phenyl, naphthyl, anthracyl, indenyl, indanyl, fluorenyl and phenanthryl. Phenyl, naphthyl and anthracyl are preferred.

R and $R^1$ can be aralkyl with preferably 7 to 14 C atoms. The aryl is preferably naphthalene and in particular benzene. The alkyl group preferably contains 1 to 3 C atoms. Examples of aralkyl are benzyl, 1-phenyleth-1-yl, 1-phenyleth-2-yl, 1-phenylprop-1-yl, -2-yl or -3-yl and 2-phenylprop-2-yl or -1-yl.

R and $R^1$ can be heteroaralkyl. Heteroaryl radicals and preferred radicals have been mentioned above. The alkyl group of the heteroaralkyl preferably contains 1–3 C atoms and is, for example, methyl, 1,1- or 1,2-ethyl or 1,1-, 2,2-, 1,2- or 1,3-propyl.

R and $R^1$ can be substituted in any desired positions by identical or different radicals, for example by 1 to 5, preferably 1 to 3, substituents.

Suitable substituents for R and $R^1$ are: $C_1$-$C_{12}$-, preferably $C_1$-$C_6$- and in particular $C_1$-$C_4$alkyl, -alkoxy or -alkylthio, for example methyl, ethyl, propyl, n-, i- and t-butyl and the isomers of pentyl, hexyl, octyl, nonyl, decyl, undecyl and dodecyl, and corresponding alkoxy and alkylthio radicals.

$C_3$-$C_6$, in particular $C_5$- or $C_6$cycloalkyl, -cycloalkoxy or -cycloalkylthio, for example cyclopentyl, cyclohexyl, cyclohexyloxy and cyclohexylthio; halogen, preferably F and Cl; CN; $C_6$-$C_{12}$aryl, -aryloxy or -arylthio, in which aryl is preferably naphthyl and in particular phenyl, $C_7$-$C_{16}$aralkyl, -aralkoxy and -aralkylthio, in which the aryl radical is preferably naphthyl and in particular phenyl and the alkylene radical is linear or branched and contains 1 to 10, preferably 1 to 6 and in particular 1–3 C atoms, for example benzyl, naphthylmethyl, 1- or 2-phenyleth-1-yl or -eth-2-yl or 1-, 2- or 3-phenyl-prop-1-yl, -prop-2-yl or -prop-3-yl, benzyl being particularly preferred;

heteroaryl or heteroaryloxy with 5 or 6 ring atoms and preferably heteroatoms from the group comprising O, S and N, the N atom being tertiary as defined above. Examples are: pyridyl, pyrimidyl, pyrryl, furyl, thienyl and pyridyloxy.

Secondary amino with 2 to 24, preferably 2 to 12 and in particular 2 to 6 C atoms, the secondary amino preferably containing 2 alkyl groups, for example dimethyl-, methylethyl-, diethyl-, methyl-n-propyl-, methyl-n-butyl-, di-n-propyl-, di-n-butyl- and di-n-hexylamino; —$CONR^2R^3$ or —$NR^2(O)CR^4$, in which $R^3$ is H, $R^2$, $R^3$ and $R^4$ independently of one another are $C_1$-$C_{12}$, preferably $C_1$-$C_6$ and in particular $C_1$-$C_4$ alkyl, phenyl or benzyl, it being possible for the alkyl to be linear or branched, for example dimethyl-, methylethyl-, diethyl-, methyl-n-propyl-, ethyl-n-propyl-, di-n-propyl-, methyl-n-butyl-, ethyl-n-butyl-, n-propyl-n-butyl- and di-n-butylcarbamoyl, and in which $R^4$ is preferably $C_1$-$C_4$-alkyl, phenyl or benzyl;

—$COOR^2$ or —$O(O)CR^4$, in which $R^2$ and $R^4$ independently of one another are $C_1$-$C_{12}$, preferably $C_1$-$C_6$alkyl, phenyl or benzyl, wherein the alkyl can be linear or branched, for example methyl, ethyl, n- and i-propyl, n-, i- and t-butyl, and the isomers of pentyl, hexyl, heptyl, octyl, nonyl, decyl, undecyl and dodecyl, and in which $R^4$ is preferably $C_1$-$C_4$alkyl, phenyl or benzyl.

The substituents alkyl, alkoxy and alkylthio can in turn be mono- or poly-substituted, in particular mono-, di- or trisubstituted, by halogen, cyano, $C_2$-$C_{24}$secondary amino, —$C(O)OR^2$, —$O(O)CR^4$, —$NR^2(O)CR^4$, —$C(O)NR^2R^3$, cycloalkyl or heterocycloalkyl with 4–8 ring C atoms or 5 or 6 ring atoms. The preferred meanings described above apply to $R^2$, $R^3$ and $R^4$. If the alkyl, alkoxy or alkylthio is substituted by halogen, preferably F and/or Cl, the radical can be, for example, $C_1$-$C_6$, preferably $C_1$-$C_4$haloalkyl, for example trifluoro- or trichloromethyl, difluorochloromethyl, fluorodichloromethyl, 1,1-difluoroeth-1-yl, 1,1-dichloroeth-1-yl, 1,1,1-trichloro- or -trifluoroeth-2-yl, pentachloroethyl, pentafluoroethyl, 1,1,1-trifluoro-2,2-dichloroethyl, n-perfluoropropyl, i-perfluoropropyl, n-perfluorobutyl, fluoro- or chloromethyl, difluoro- or dichloromethyl, 1-fluoro- or -chloroeth-2-yl or -eth-1-yl, 1-, 2- or 3-fluoro- or -chloro-prop-1-yl or -prop-2-yl or -prop-3-yl, 1-fluoro- or -chloro-but-1-yl, -but-2-yl, -but-3-yl, or -but-4-yl, 2,3-dichloro-prop-1-yl, 1-chloro-2-fluoro-prop-3-yl or 2,3-dichlorobut-1-yl.

Examples of alkyl, alkoxy or alkylthio substituted by cyano are cyanomethyl, 1- or 2-cyanoethyl, 1- or 2-cyanopropyl and 2-cyanoethyloxy. If the alkyl, alkoxy or alkylthio is substituted by —$C(O)OR^2$, —$O(O)CR^4$, —$NR^2(O)CR^4$ or —$C(O)NR^2R^3$, it preferably contains 1 to 3 C atoms.

Examples are methoxy- or ethoxycarbonylmethyl, 1- or 2-methoxy- or -ethoxycarbonylethyl, 1-, 2- or 3-methoxy- or -ethoxycarbonylpropyl, acetyloxymethyl, 1- or 2-acetyloxyethyl, dimethylaminocarbonylmethyl or -ethyl, N-methylacetylamino, methoxycarbonylmethoxy or 1-(methoxycarbonyl)eth-2-oxy.

If the alkyl, alkoxy and alkylthio are substituted by cycloalkyl or heterocycloalkyl, the cycloalkyl preferably contains 5 or 6 ring C atoms and the heterocycloalkyl 5 or 6 ring atoms and preferably heteroatoms from the group comprising O, N and S, in particular O, the N atom being tertiary. Examples are cyclohexylmethyl or -methoxy or -methylthio, cyclopentylethyl, tetrahydrofurylmethyl and pyridylmethyl.

The substituents cycloalkyl, cycloalkoxy, cycloalkylthio, aryl, aryloxy, arylthio, aralkyl, aralkoxy, aralkylthio, heteroaryl and heteroaryloxy can in turn be substituted as defined for alkyl, alkoxy and alkylthio and can additionally be mono- or polysubstituted, in particular mono-, di- or trisubstituted, by $C_1$-$C_{12}$, in particular $C_1$-$C_6$alkyl or -alkylthio. Examples are methylcyclohexyl, -hexoxy and -hexylthio, methylphenyl, dimethylphenyl, methylchlorophenyl, cyanophenyl, chlorophenoxy, dichlorophenoxy, trifluoromethylphenyl or -phenoxy, methoxyphenyl or -phenoxy, fluoro- or difluorophenyl or -phenoxy, chlorobenzyl or -benzyloxy, methyl- or dimethylbenzyl, carbomethoxyphenyl, methoxybenzyl, chloro- or dichloropyrridyl, methylpyrridyl, methylpyrridyloxy, and chloro- or dichloropyrridyloxy.

A preferred group of substituents for R and $R^1$ is $C_1$-$C_6$alkyl, -halogenalkyl and -alkoxy, $C_1$-$C_6$alkoxy-$C_1$-$C_3$alkyl and -alkoxy, $C_1$-$C_6$cyanoalkyl, $C_1$-$C_4$alkyl O(O)$C_1$-$C_6$alkyl, $C_6$-$C_{12}$-aryl- and -aryloxy, $C_7$-$C_{16}$ alkaryl and -alkaryloxy, fluoro- and/or chloroaryl and -aryloxy, trifluoromethylaryl and -aryloxy, $C_1$-$C_6$alkoxyaryl and -aryloxy, $C_8$-$C_{16}$alkaralkyl and -alkaralkyloxy, fluoro- and/or chloro- and/or trifluoromethyl-$C_7$-$C_{12}$-aralkyl and -aralkoxy, $C_7$-$C_{12}$aralkyl, pyrridyl, pyrridyloxy and fluoroand/or chloropyrridyl and -pyrridyloxy.

In a preferred embodiment, R and $R^1$ in formula I are the same radicals. In another preferred embodiment, in formula I R is unsubstituted or substituted $C_6$-$C_{10}$aryl and $R^1$ is linear or branched $C_1$-$C_{12}$alkyl.

In another preferred embodiment, R and $R^1$ in formula I independently of one another are unsubstituted or substituted $C_1$-$C_{12}$alkyl, $C_2$-$C_6$-alkenyl or -alkynyl, $C_4$-$C_8$cycloalkyl or -cycloalkenyl, heterocycloalkyl or heterocycloalkenyl with 4 to 8 ring atoms, a polycyclic radical with 6-10 C atoms, $C_6$-$C_{10}$aryl, $C_7$-$C_{16}$aralkyl, heteroaryl with 5 or 6 ring atoms or heteroaralkyl with 5 or 6 atoms and 1 or 2 C atoms in the alkyl group.

In a particularly preferred embodiment, R and $R^1$ in formula I independently of one another are substituted or unsubstituted $C_1$-$C_{18}$alkyl, $C_2$-$C_{18}$alkenyl, $C_3$-$C_{10}$cycloalkyl, $C_6$-$C_{14}$aryl or $C_7$-$C_{16}$aralkyl.

Thioureas of the formula II are known or can be prepared by generally known processes.

The photooxidation can be carried out, for example, with light with a wavelength of preferably 200 to 700 nm. If UV light is used, for example in the UV-B range, the additional use of sensitizers can be dispensed with. It has proved advantageous to carry out the photooxidation with UV light or visible light in the presence of a sensitizer. Suitable light sources are, for example, sunlight, halogen lamps, incandescent lamps for exposure from the outside, sodium vapour lamps or mercury vapour lamps (as a UV light source).

Suitable sensitizers for producing singlet oxygen are, for example: xanthene dyes (Bengal pink), thiazines (methylene blue), porphyrins (tetraphenylporphyrin), thionine, eosine, erythrosine, phenosafranine, chlorophyll, flavines, thioxanthones, phthalocyanines, thiophenes, naphthalene derivatives, phenothiazines, pyrazolanthrones, ketocoumarins, azines (riboflavin), anthraquinones, metallocenes, benzophenones and anthracene derivatives. A preferred group is methylene blue, Bengal pink, tetraphenylporphyrin and phthalocyanines.

The reaction can be carried out at a temperature of, for example, −20° C. to 50° C., preferably at room temperature (about 15° C. to 35° C.).

Suitable solvents are inert organic solvents and solvent mixtures and mixtures thereof with water. Suitable solvents are, for example, aliphatic, cycloaliphatic and aromatic hydrocarbons (pentane, hexane, cyclohexane, benzene and toluene), chlorohydrocarbons (methylene chloride, chloroform, carbon tetrachloride, tri- or tetrachloroethane and chlorobenzene), alcohols (methanol, ethanol and ethylene glycol monomethyl ether), ethers (diethyl ether, dibutyl ether, ethylene glycol diethyl ether, tetrahydrofuran and dioxane), ketones (methyl isobutyl ketone), esters (ethyl acetate), nitriles (acetonitrile), N,N-disubstituted carboxylic acid amides and lactams (dimethylacetamide and N-methylpyrrolidone) and sulfones (tetramethylene sulfone). A preferred solvent is a mixture of acetonitrile and water.

Sulfuric acid is formed in the reaction. At least 2 equivalents, for example 2 to 2.5 equivalents, of the acid-trapping agent are therefore advantageously used.

The acid-trapping agent can be, for example, an alkali metal base or alkaline earth metal base, an alkali metal carbonate or alkali metal bicarbonate or a buffer solution with a pH$\geq$7. Examples are LiOH, KOH, NaOH, Ca(OH)$_2$, NaHCO$_3$, CaHCO$_3$ and KHCO$_3$. Suitable buffer mixtures with a pH$\geq$7 are, for example, aqueous solutions of borax/NaCl or KH$_2$PO$_4$, K$_3$PO$_4$, borax, NaHCO$_3$, Na$_2$HPO$_4$ or KCl and NaOH. NaOH is preferably used.

The process can be carried out by passing gaseous oxygen, for example pure oxygen, air or oxygen mixed with inert gases, into the reaction mixture. Inert gases are, for example, nitrogen, carbon dioxide and noble gases, for example helium, neon and argon. The use of singlet oxygen is preferred, especially if sensitizers are additionally used.

In detail, the process according to the invention can be carried out by a procedure in which the compound of the formula I, the acid-trapping agent, the solvent and if appropriate the sensitizer are taken and the mixture is stirred thoroughly in an open system in the presence of air, while being exposed to light, or oxygen or an oxygen/inert gas mixture is passed through the reaction mixture while the mixture is stirred and exposed to light.

The reaction mixture is worked up in the customary manner, for example by extraction, washing and drying of the extract and removal of the solvent by distillation. The carbodiimides of the formula I thus obtainable can be further purified by distillation, crystallization or chromatographic methods.

The carbodiimides are obtained in high yields in surprisingly short reaction times by the process according to the invention. One advantage is that the photooxidation can be carried out in aqueous solutions.

The carbodiimides of the formula I can be converted into cyanoguanidines with cyanamide in a manner which is known per se, the products being suitable as latent curing agents for, for example, epoxy resins.

The following examples illustrate the invention in more detail.

(A) Preparation Examples

Examples 1–12

(a) 3.0 g (14.4 mmol) of N-phenyl-N'-t-butylthiourea, 1.28 g (32.0 mmol) of NaOH and 30 mg (0.2 mol %) of Bengal pink are dissolved in a mixture of 130 ml of acetonitrile and 15 ml of water. The mixture is exposed to a 100 W Philips halogen lamp for 1.5 hours, while stirring vigorously and under an air atmosphere. The lamp is immersed in the reaction solution in a double-walled water-cooled glass shaft. The mixture is then extracted with 4×200 ml of pentane, the organic phase is washed 2× with water and 1× with saturated NaCl solution, dried over MgSO$_4$ and concentrated on a rotary evaporator and the residue is distilled in a bulb tube under a high vacuum.

(a') The procedure is as in a) but methylene blue is used instead of Bengal pink and a sodium vapour lamp is used instead of the halogen lamp.

(b) The procedure is as in (a), but phosphate buffer of pH 7 is used instead of NaOH. The $CH_3CN-H_2O$ ratio is 2.3:1. The solution is 0.01 molar in thiourea. 2 mol % of Bengal pink are furthermore used.

(c) The procedure is as in (b), but cyclohexane or pentane (about 40% of the reaction volume) is additionally added to the aqueous acetonitrile solution ($CH_3CN-H_2O$ 4:1). The solution is 0.02–0.05 molar in thiourea and 1.5 mol % of Bengal pink is used. The results are summarized in Table 1.

| Example | R (in R—N=C=N—R¹) | R¹ | Yield [%] | IR(CHCl₃) [cm⁻¹] |
|---|---|---|---|---|
| 1[a] | 2,6-diisopropyl-4-phenoxyphenyl (with CH₃, CH₃ substituents) | t-C₄H₉ | 91 | 2145 |
| 2[a'] | dichloro-pyridinyl-oxy-dimethylphenyl | t-C₄H₉ | 88 | 2145 |
| 3[a] | phenyl | t-C₄H₉ | 83 | 2125 |
| 4[a] | " | cyclohexyl | 71 | 2140 |
| 5[c] | " | n-C₄H₉ | 71 | 2145 |
| 6[b] | " | —CH₂CH₂COOCH₃ | 31 | 1735, 2145 |
| 7[b] | " | phenyl | 37 | 2140 |
| 8[a] | cyclohexyl | cyclohexyl | 57 | 2120 |
| 9[c] | n-C₄H₉ | n-C₄H₉ | 81 | 2130 |
| 10[b] | phenyl | 2,6-dimethylphenyl | 66 | 2145 |
| 11[b] | " | CH₂=CHCH₂— | 40 | 2140 |
| 12[b] | CH₂=CHCH₂— | CH₂=CHCH₂— | 41 | 2145 |
| 13[a] | phenyl | 1-Adamantyl | 91 | 2110, 2135 S |

-continued

| Example | R (R—N=C=N—R¹) | R¹ | Yield [%] | IR(CHCl₃) [cm⁻¹] |
|---|---|---|---|---|
| 14[c] | 4-cyanophenyl | phenyl | 46 | 2140 |
| 15[a] | benzyl (C₆H₅–CH₂–) | phenyl | 58 | 2130 |
| 16[a] | 2-naphthyl | phenyl | 22 | 2130 |
| 17[a] | morpholino–CH₂–CH₂– | phenyl | 53 | 2130 |
| 18[a] | 2-pyridyl | phenyl | 41 | 2140 |
| 19[a] | C₆H₅–N(CHO)–(2,4,6-triisopropylphenyl) | t-C₄H₉ | 74 | 2140, 1675 |
| 20[a] | 2-naphthyl (decahydro?) | t-C₄H₉ | 87 | 2120 |

Use Examples

Examples 21–22: The carbodiimides of Examples 7 and 8 are heated under reflux in 1,2-dichloroethane with cyanamide for 16 hours. The mixture is evaporated until a suspension is obtained, the suspension is stirred with ether and the crystalline compounds are filtered off with suction. N-Cyano-N',N''-diphenylguanidine (I, melting point: 198°–199° C.) or N-cyano-N',N''-dicyclohexylguanidine (II, melting point: 191° C.) is obtained.

15 g of the cyanoguanidines are in each case mixed with 100 g of a bisphenol A diglycidyl ether (epoxide content 5.4 equivalents/kg) and the mixture is cured at 180° C. for 4 hours. Clear cast bodies with the glass transition temperature (Tg, determined by means of DSC) shown in Table 2 are thereby formed:

| Example | Compound No. | Tg (°C.) |
|---|---|---|
| 21 | I | 145 |
| 22 | II | 129 |

What is claimed is:

1. A process for the preparation of carbodiimide of the formula I

in which

R and $R^1$ independently of one another are $C_1$–$C_{20}$alkyl, $C_2$–$C_{18}$alkenyl, or $C_2$–$C_{18}$alkynyl; $C_3$–$C_{10}$cycloalkyl, $C_3$–$C_{10}$cycloalkenyl, heterocyclyl which has 3 to 10 ring atoms and is bonded via a C atom, heterocycloalkenyl which has 3 to 10 and is bonded via a C atom, a polycyclic hydrocarbon radical with 6 to 10 atoms, $C_6$–$C_{14}$aryl, $C_7$–$C_{20}$aralkyl, heteroaryl with 5 or 6 ring atoms or heteroaralkyl with 5 to 6 ring atoms and 1 to 6 C atoms in the alkyl group, which cyclic groups are unsubstituted or substituted by $C_1$–$C_{12}$alkyl, $C_1$–$C_{12}$alkoxy, $C_1$–$C_{12}$alkylthio, $C_3$–$C_6$cycloalkyl, $C_3$–$C_6$cycloalkoxy $C_3$–$C_6$cycloalkylthio, $C_6$–$C_{10}$aryl, $C_6$–$C_{10}$aryloxy, $C_6$–$C_{10}$arylthio, $C_7$–$C_{16}$aralkyl, $C_7$–$C_{16}$aralkoxy, $C_7$–$C_{16}$aralkylthio, heteroaryl with 5 or 6 ring atoms, heteroaryloxy with 5 or 6 ring atoms, cyano, halogen, $C_2$–$C_{24}$secondary amino, —C(O)OR$^2$, —O(O)CR$^4$, —NR$^2$(O)CR$^4$ or —C(O)NR$^2$R$^3$;

$R^2$ and $R^4$ independently from each other are $C_1$–$C_{12}$alkyl, phenyl or benzyl;

$R^3$ is hydrogen $C_1$–$C_{12}$alkyl, phenyl or benzyl;

it being possible for the substituents $C_1$–$C_{12}$alkyl, $C_1$–$C_{12}$alkoxy and $C_1$–$C_{12}$ alkylthio in turn to be substituted by $C_1$–$C_{12}$alkoxy, halogen, cyano, $C_2$–$C_{24}$secondary amino, —C(O)OR$^2$, —O(O)CR$^4$, —NR$^2$(O)CR$^4$, —C(O)NR$^2$R$^3$, cycloalkyl or heterocycloalkyl with 4–8 ring C atoms or 5 or 6 ring atoms, and for the substituents cycloalkyl, cycloalkoxy, cycloalkylthio, aryl, aryloxy, arylthio, aralkyl, aralkoxy, aralkylthio, heteroaryl or heteroeryloxy to be substituted by $C_1$–$C_{12}$alkyl, -alkoxy or -alkylthio, halogen, cyano, $C_2$–$C_{24}$secondary amino, —C(O)OR$^2$, —O(O)CR$^4$, —NR$^2$(O)CR$^4$, —C(O)NR$^2$R$^3$, and it being possible for cycloalkyl, cycloalkenyl, heterocycloalkyl or heterocycloalkenyl as defined for R and $R^1$ to be fused with $C_6$–$C_{14}$aryl or heteroaryl with 5 or 6 ring atoms, by photooxidation of a thiourea of the formula II

in which R and $R^1$ are as defined above with oxygen in a solvent, which comprises carrying out the reaction in the presence of an acid trapping agent which is soluble in the reaction medium.

2. The process according to claim 1, wherein the photooxidation is carried out with UV light or visible light in the presence of a sensitizer.

3. The process according to claim 2, wherein the sensitizer is methylene blue, Bengal pink or a phthalocyanine.

4. The process according to claim 1, carried out at a temperature of −20° C. to 50° C.

5. The process according to claim 1, carried out in an organic solvent, a solvent mixture or a mixture thereof with water.

6. The process according to claim 1, wherein at least 2 equivalents of the acid-trapping agent are used per mol of thiourea of the formula II.

7. The process according to claim 1, wherein the acid-trapping agent is an alkali metal base or alkaline earth metal base, an alkali metal carbonate or bicarbonate or a buffer solution with a pH≧7.

8. The process according to claim 7, wherein the solvent is a mixture of acetonitrile and water.

9. The process according to claim 1, carried out with pure oxygen, air or a mixture of oxygen with an inert gas.

10. The process according to claim 9, wherein the inert gas is nitrogen, carbon dioxide or a noble gas.

11. The process according to claim 1, wherein R and $R^1$ are identical radicals.

12. The process according to claim 1, wherein R and $R^1$ in formula I independently of one another are unsubstituted or substituted, as defined in claim 1, $C_1$–$C_{12}$alkyl, $C_2$–$C_6$alkenyl or -alkynyl, $C_4$–$C_8$cycloalkyl or -cycloalkenyl, heterocycloalkyl or heterocycloalkenyl with 4 to 8 ring atoms, a polycyclic radical with 6–10 C atoms, $C_6$–$C_{10}$aryl, $C_7$–$C_{16}$-aralkyl, heteroaryl with 5 or 6 ring atoms or heteroaralkyl with 5 or 6 ring atoms and 1 or 2 C atoms in the alkyl group.

13. The process according to claim 12, wherein in formula I R is unsubstituted or substitued $C_6$–$C_{10}$aryl and $R^1$ is linear or branched $C_1$–$C_{12}$alkyl.